United States Patent
Kwatra et al.

(10) Patent No.: US 11,671,406 B2
(45) Date of Patent: Jun. 6, 2023

(54) PATTERNED AND CORRELATED ELECTRICAL ACTIVITY

(71) Applicant: International Business Machines Corporation, Armonk, NY (US)

(72) Inventors: Shikhar Kwatra, San Jose, CA (US); Liam S. Harpur, Dublin (IE); Jeremy R. Fox, Georgetown, TX (US); Sarbajit K. Rakshit, Kolkata (IN)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 210 days.

(21) Appl. No.: 17/087,697

(22) Filed: Nov. 3, 2020

(65) Prior Publication Data

US 2022/0141196 A1    May 5, 2022

(51) Int. Cl.
| | |
|---|---|
| *G08B 1/08* | (2006.01) |
| *H04L 9/40* | (2022.01) |
| *A61B 5/00* | (2006.01) |
| *G16H 50/30* | (2018.01) |
| *G16H 50/70* | (2018.01) |
| *A61B 5/11* | (2006.01) |

(52) U.S. Cl.
CPC ........ *H04L 63/0421* (2013.01); *A61B 5/7282* (2013.01); *G16H 50/30* (2018.01); *G16H 50/70* (2018.01); *A61B 5/1123* (2013.01)

(58) Field of Classification Search
CPC .... H04L 63/0421; G16H 50/30; G16H 50/70; A61B 5/7282; A61B 5/1123
See application file for complete search history.

(56) References Cited

U.S. PATENT DOCUMENTS

| | | | |
|---|---|---|---|
| 9,078,598 B2 | 7/2015 | French et al. | |
| 9,763,592 B2 | 9/2017 | Le et al. | |
| 10,188,347 B2* | 1/2019 | Self | A61B 5/4866 |
| 10,413,218 B2* | 9/2019 | Yamato | A61B 5/6824 |
| 10,571,999 B2 | 2/2020 | Tanaka et al. | |
| 10,846,745 B1* | 11/2020 | Meissner | G06Q 30/0267 |
| 10,923,224 B2* | 2/2021 | Sasaki | A63B 69/3667 |
| 11,342,051 B1* | 5/2022 | Jain | G16H 10/60 |
| 11,363,069 B1* | 6/2022 | Becker | H04L 63/10 |
| 2003/0009603 A1 | 1/2003 | Ruths et al. | |
| 2005/0234310 A1* | 10/2005 | Alwan | A61B 5/1112 128/920 |

(Continued)

OTHER PUBLICATIONS

Chunana et al., Why We Need Crowdsourced Data in Infectious Disease Surveillance (Year: 2013).*

(Continued)

*Primary Examiner* — Quang Pham
(74) *Attorney, Agent, or Firm* — Cantor Colburn LLP; Erik Johnson

(57) ABSTRACT

Techniques for patterned and correlated electrical activity include receiving user data from a device of a user and anonymized data from other devices of other users, the user data and the anonymized data being received based on the device and the other devices having been co-located. The user data is compared to the anonymized data according to an activity. It is determined that an event occurred based on one or more deviations of the user data from the anonymized data according to the activity, the event being related to a health of the user.

14 Claims, 11 Drawing Sheets

(56) References Cited

U.S. PATENT DOCUMENTS

| | | | |
|---|---|---|---|
| 2008/0216125 A1 | 9/2008 | Li et al. | |
| 2010/0302041 A1* | 12/2010 | Malik | G08B 21/04 |
| | | | 340/573.1 |
| 2011/0291827 A1* | 12/2011 | Baldocchi | G08B 21/0476 |
| | | | 340/539.11 |
| 2013/0041590 A1* | 2/2013 | Burich | G16H 40/63 |
| | | | 702/19 |
| 2013/0198292 A1 | 8/2013 | Aaltonen et al. | |
| 2013/0317384 A1* | 11/2013 | Le | G16H 20/70 |
| | | | 600/545 |
| 2014/0302783 A1* | 10/2014 | Aiuto | G01S 5/0284 |
| | | | 455/67.11 |
| 2014/0309941 A1* | 10/2014 | Bardy | G16H 10/60 |
| | | | 702/19 |
| 2016/0007165 A1* | 1/2016 | Somer | H04W 4/029 |
| | | | 455/404.2 |
| 2016/0038093 A1* | 2/2016 | Sharma | A61B 5/4836 |
| | | | 600/481 |
| 2016/0125747 A1* | 5/2016 | Chou | G16H 10/60 |
| | | | 434/236 |
| 2017/0005958 A1* | 1/2017 | Frenkel | G01S 5/0242 |
| 2017/0012972 A1* | 1/2017 | Tanaka | G06F 1/1698 |
| 2017/0061817 A1 | 3/2017 | Mettler May | |
| 2017/0087412 A1* | 3/2017 | Blahnik | G06Q 10/10 |
| 2017/0318360 A1* | 11/2017 | Tran | A63F 13/245 |
| 2017/0323155 A1* | 11/2017 | Biswas | G01S 15/86 |
| 2017/0372216 A1* | 12/2017 | Awiszus | A61F 11/06 |
| 2018/0271454 A1* | 9/2018 | Kramer | A61B 5/7405 |
| 2018/0285986 A1* | 10/2018 | Perry | H04L 51/52 |
| 2018/0336970 A1* | 11/2018 | Sherwood | A61B 5/082 |
| 2018/0366221 A1* | 12/2018 | Crehore | G06F 16/211 |
| 2019/0087908 A1* | 3/2019 | Kita | G16H 20/10 |
| 2019/0133470 A1* | 5/2019 | Szabados | A61B 5/02405 |
| 2019/0175411 A1* | 6/2019 | Awiszus | A41D 13/12 |
| 2019/0236923 A1* | 8/2019 | Devdas | A61B 5/1118 |
| 2019/0339753 A1* | 11/2019 | Shabbir | H05K 7/20136 |
| 2019/0373068 A1* | 12/2019 | Cun | H04L 51/046 |
| 2020/0004655 A1* | 1/2020 | Abrami | G06N 20/00 |
| 2020/0020447 A1* | 1/2020 | Generoso | G16H 50/70 |
| 2020/0085300 A1* | 3/2020 | Kwatra | G16H 20/00 |
| 2020/0099545 A1* | 3/2020 | Hong | H04L 12/2803 |
| 2020/0111341 A1* | 4/2020 | Zhao | G06V 40/23 |
| 2020/0124588 A1* | 4/2020 | Peterson | G01N 33/6896 |
| 2020/0155058 A1* | 5/2020 | Rakshit | A61B 5/4362 |
| 2020/0155078 A1* | 5/2020 | Mei | G06N 3/08 |
| 2020/0315549 A1* | 10/2020 | Usui | G16H 40/63 |
| 2020/0320574 A1* | 10/2020 | Levy | H04W 4/23 |
| 2020/0320895 A1* | 10/2020 | Yang | G09B 5/06 |
| 2020/0350076 A1* | 11/2020 | Brown | G16H 10/20 |
| 2020/0397355 A1* | 12/2020 | Kuhn | A61B 5/1118 |
| 2020/0403951 A1* | 12/2020 | Kapoor | H04L 51/216 |
| 2021/0000374 A1* | 1/2021 | Le | G16H 50/20 |
| 2021/0007874 A1* | 1/2021 | Galiana Bujanda | A61F 5/028 |
| 2021/0050085 A1* | 2/2021 | Hayter | A61B 5/7267 |
| 2021/0082265 A1* | 3/2021 | Sequeira | G06N 20/00 |
| 2021/0183486 A1* | 6/2021 | Sakurada | G16H 50/70 |
| 2021/0243265 A1* | 8/2021 | Hammond | H04L 67/535 |
| 2021/0366603 A1* | 11/2021 | Kåberg Johard | G16H 40/63 |
| 2022/0028546 A1* | 1/2022 | Bilal | A61B 5/1101 |
| 2022/0068499 A1* | 3/2022 | Tadesse | G16H 50/50 |
| 2022/0166621 A1* | 5/2022 | Kairon | G16H 10/60 |
| 2022/0284824 A1* | 9/2022 | Gerson | A61B 5/6898 |
| 2022/0301407 A1* | 9/2022 | Nagy | A61B 5/6801 |
| 2022/0319508 A1* | 10/2022 | Furman | G06F 40/30 |

OTHER PUBLICATIONS

Kerri Wazny, Applications of crowdsourcing in health an Overview (Year: 2016).*

Konvalinka et al., Synchronized arousal between performers and related spectators in a fire-walking ritual (Year: 2011).*

Alam, M. et al., "AutoCogniSys: IoT Assisted Context-Aware Automatic Cognitive Health Assessment," May 17, 2020, arXiv preprint arXiv: 2003.07492, 11 pages.

Edge Computing Market Worth $43.4 Billion by 2027, CAGR: 37.4%, retrieved Sep. 15, 2020, pp. 1-7, https://www.grandviewresearch.com/press-release/global-edge-computing-market.

Le, M., "Universal Mobile Service Execution Framework for Device-to-Device Collaborations," May 2018, Utah State University, DigitalCommons@USU, All Graduate Theses and Dissertations, Graduate Studies, 7032, https://digitalcommons.usu.edu/etd/7032, 169 pages.

Mihovska, A. & Sarkar, M., "Cooperative Human-Centric Sensing Connectivity," 2018, In Internet of Things—Technology, Applications nd Standardiztion, IntechOpen, 20 pages.

Tan, H. et al., "Early Detection of Mild Cognitive Impairment in Elderly Through IoT: Preliminary Findings," Feb. 2018, Singapore Management University, Institutional Knowledge at Singapore Mangement University, Research Collection of School Information Systems, School of Information Systems, In 2018 IEEE 4th World Forum on Internet of Things (WF-IoT), 9 pages.

Urwyler, P. et al., "Cognitive impairment categorized in community-dwelling older adults with and without dementia using in-home sensors that recognise activities of daily living," Feb. 8, 2017, Scientific Reports, vol. 7, No. 42084, 9 pages.

* cited by examiner

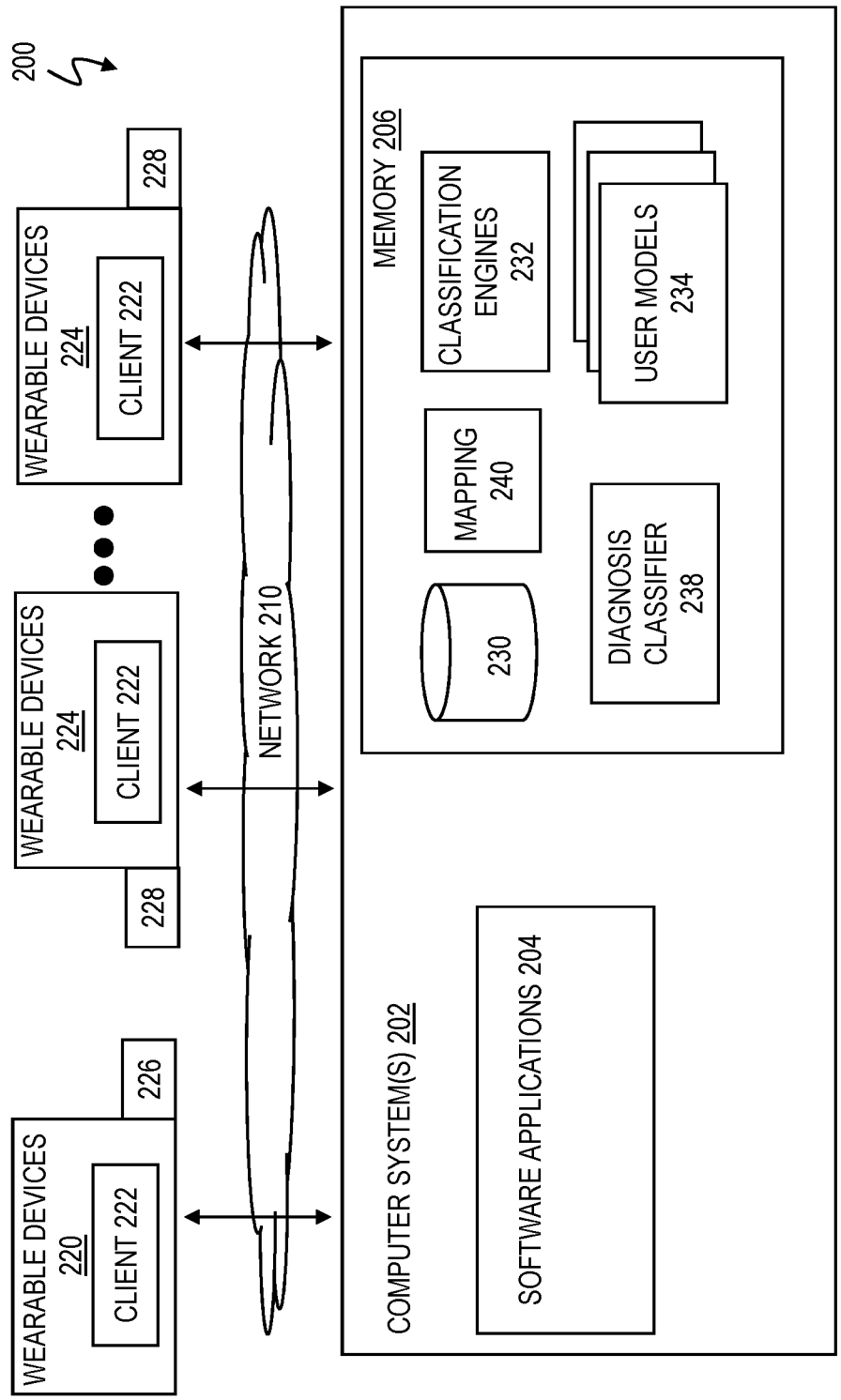

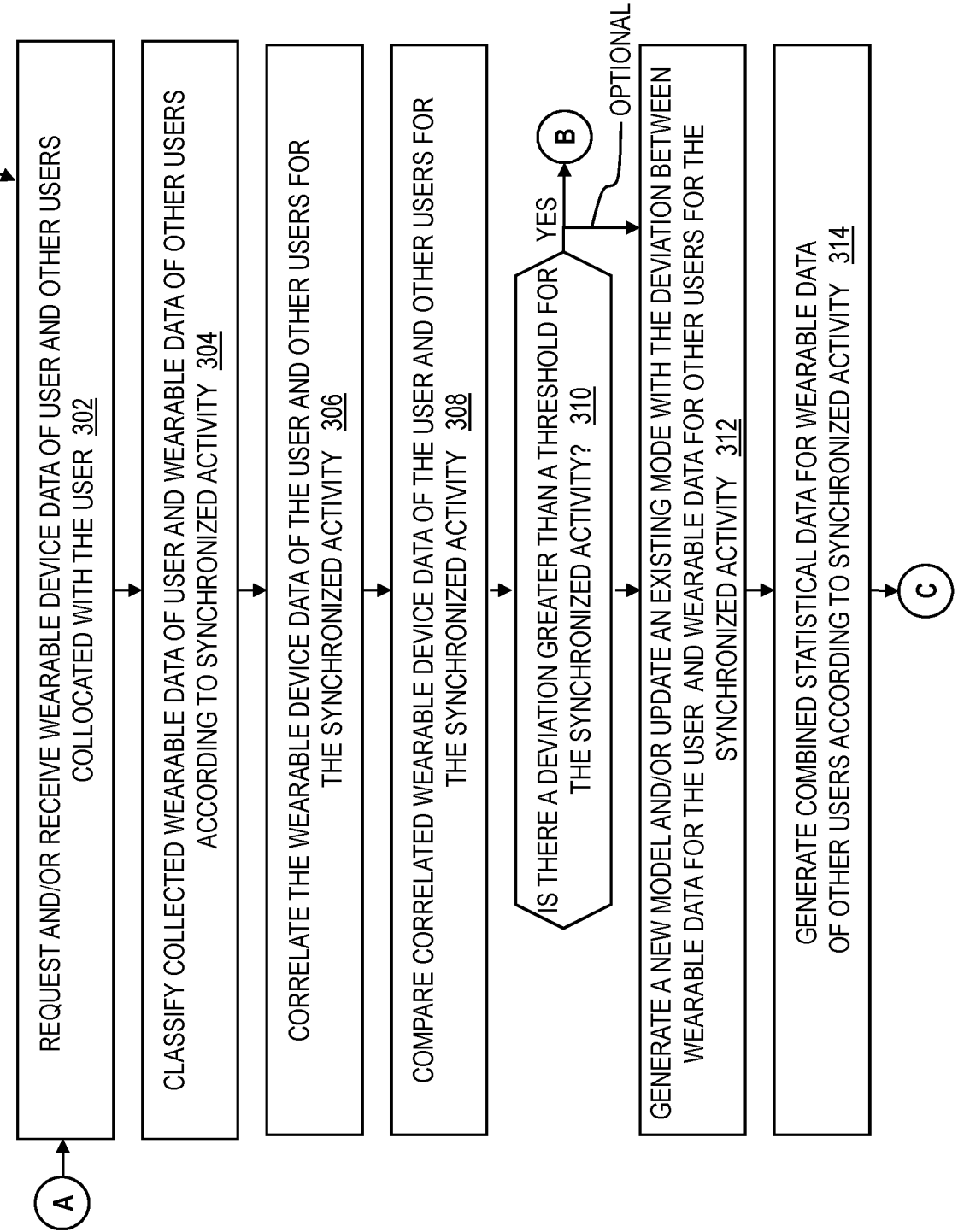

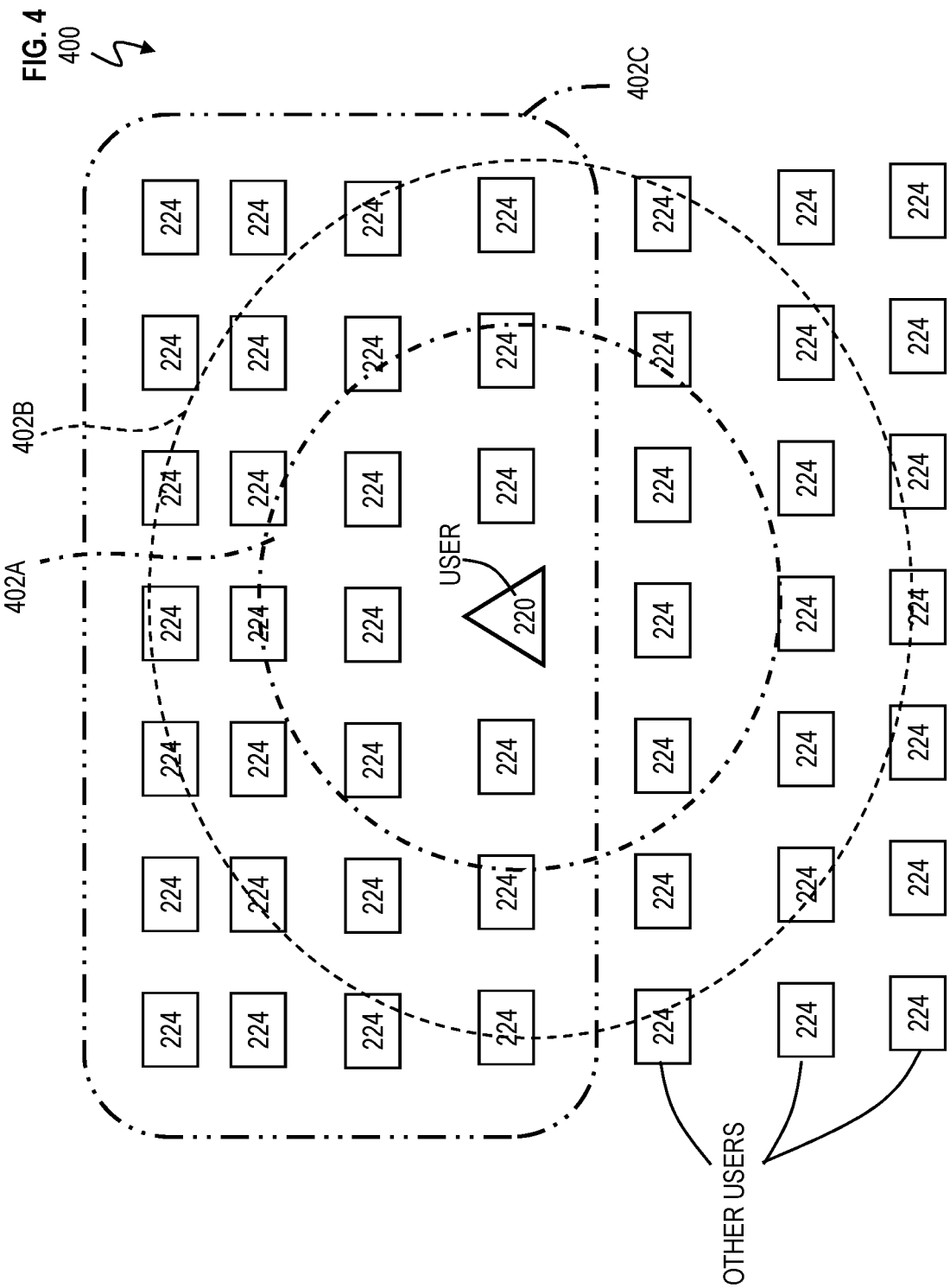

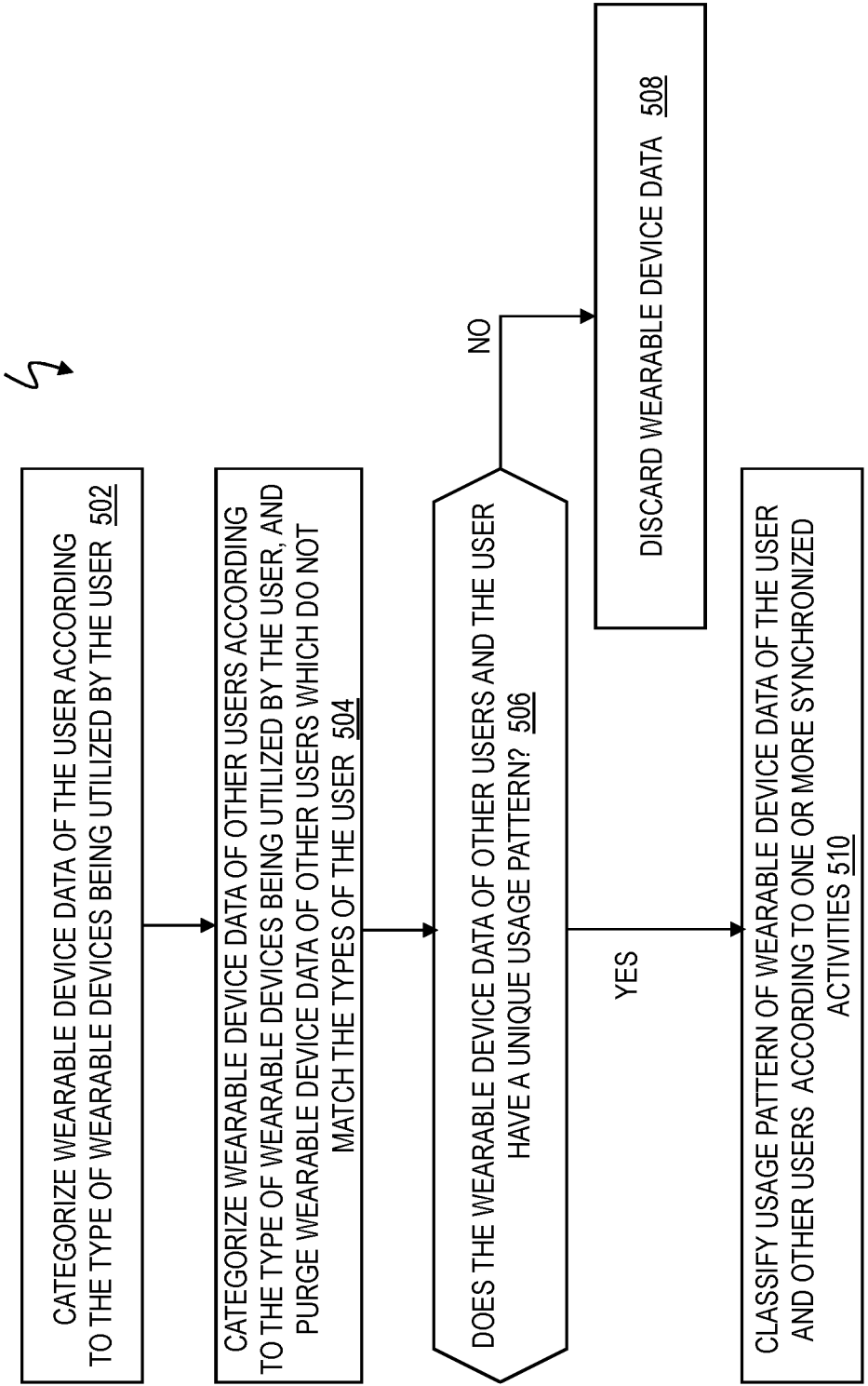

FIG. 6
600

| ANONYMIZED DEVICE ID | HJDFJ-988-SF |
|---|---|
| TIME(S) AND MEASURED OUTPUT | t0 X UNITS (E.G., METERS); t1 Y UNITS; t2 Z UNITS; ETC. |
| USE LOCATION? | YES. DEFAULT TO GEOFENCE 34882305 |
| EXACT TIMING | YES. NLS_DATE_FORMAT = "YYYY-MM-DD HH24:MI:SS" |
| ACTIVITY TO TRACK | E.G., SPEAKING; LEG MOVEMENT; HEAD MOVEMENT; HAND/ARM MOVEMENT, ETC. |

OUTPUT

PATTERNED AND CORRELATED ELECTRICAL ACTIVITY

BACKGROUND

The present invention generally relates to computer systems, and more specifically, to computer systems, computer-implemented methods, and computer program products for patterned and correlated electrical activity.

Wearable technology, wearables, fashion technology, smartwear, tech togs, skin electronics or fashion electronics are smart electronic devices, for example, with microcontrollers, that are worn close to and/or on the surface of the skin. The wearable technology or wearable devices detect, analyze, and transmit information concerning, for example, body signals such as vital signs, and/or ambient data and allow in some cases immediate biofeedback to the wearer. Wearable devices such as activity trackers are an example of the Internet of Things (IoT), since "things" such as electronics, software, sensors, and connectivity are effectors that enable objects to exchange data through the internet with a manufacturer, operator, and/or other connected devices, without requiring human intervention. Wearable technology has a variety of applications which grows as the field itself expands.

Wearable devices include wearable health devices (WHDs) which are increasingly helping people to better monitor their health status both at an activity/fitness level for self-health tracking and at a medical level providing more data to clinicians with a potential for earlier diagnostic and guidance of treatment. Some of the simplest and original forms of wearable technology are wearable fitness trackers, which are wristbands equipped with sensors to keep track of the user's physical activity and heart rate. Wearable fitness trackers provide wearers with health and fitness recommendations by connecting to various smartphone applications.

SUMMARY

Embodiments of the present invention are directed to patterned and correlated electrical activity. A non-limiting example computer-implemented method includes receiving user data from a device of a user and anonymized data from other devices of other users, the user data and the anonymized data being received based on the device and the other devices having been co-located. The method includes comparing the user data to the anonymized data according to an activity and determining that an event occurred based on one or more deviations of the user data from the anonymized data according to the activity, the event being related to a health of the user.

Other embodiments of the present invention implement features of the above-described method in computer systems and computer program products.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

FIG. 2 depicts a block diagram of a system for using patterned and correlated electrical activity or data of a user and other users to determine a medical event for the user in accordance with one or more embodiments of the present invention;

FIGS. 3A and 3B together depict a flowchart of a process for using patterned and correlated electrical activity or data of a user and other users to determine a medical event for the user in accordance with one or more embodiments of the present invention;

FIG. 4 depicts a block diagram of an example social interaction area in accordance with one or more embodiments of the present invention;

FIG. 5 is a flowchart of a computer-implemented process for classifying wearable device data of the user and other users responsive to and/or concurrent with the process in FIGS. 3A and 3B in accordance with one or more embodiments of the present invention;

FIG. 6 depicts an example of wearable device data in a structured format in accordance with one or more embodiments of the present invention;

DETAILED DESCRIPTION

One or more embodiments of the present invention provide techniques to identify and correlate electrical patterns at the edge of network(s) through personal devices and utilize those patterns to investigate an individual's behavior for triggers related to health issues. One or more embodiments identity when a user is not in synchronization with a larger group of co-located users using, for example, edge computing techniques. Through behavior mapping, tracking, identification, and finally remediation, one or more embodiments can predict that the user is experiencing a medical event pertaining to an onset of degradation and/or degradation of synchronization within human behavior, further using the degradation of synchronization to predict more serious future medical issues.

Multiple people can perform synchronized interactions with each other in a subconscious manner such as, for example, clapping along with other people in a crowd, walking in a group, singing in a choir, chanting at a sports event, etc. A user will subconsciously synchronize his/her activity with others. In this case, the brain of a person tends to act in a unanimous fashion, for example, following or participating in clapping with multiple people to create a rhythm, engaging in synchronized body movement among multiple people (which helps people to walk together in a group), moving a body part such as an arm or hand in a synchronized manner at a sports event, etc. As such, what the user sees and hears are processed by the brain, and the brain via the nervous system sends a signal to the muscular system to perform physical activity. In this scenario, if the user is not able to synchronize his/her activity with others, then there is a problem of cognitive imbalance which is not allowing the user to perform the activity in a synchronized manner as can be determined according to one or more embodiments; in some cases, this can be a problem that develops gradually and/or can be problem that develops instantaneously, for example during or after a stroke. In accordance with one or more embodiments, systems and methods track and detect any type of problem with synchronized activity for both medical problems that develop gradually over time and medical problems that have a rapid onset. As a result of the detection of a medical problem, the system alerts the user to immediately consult a doctor and take an ameliorative action. Additionally, a medical professional can be alerted of the medical condition of the user.

Figure 1:
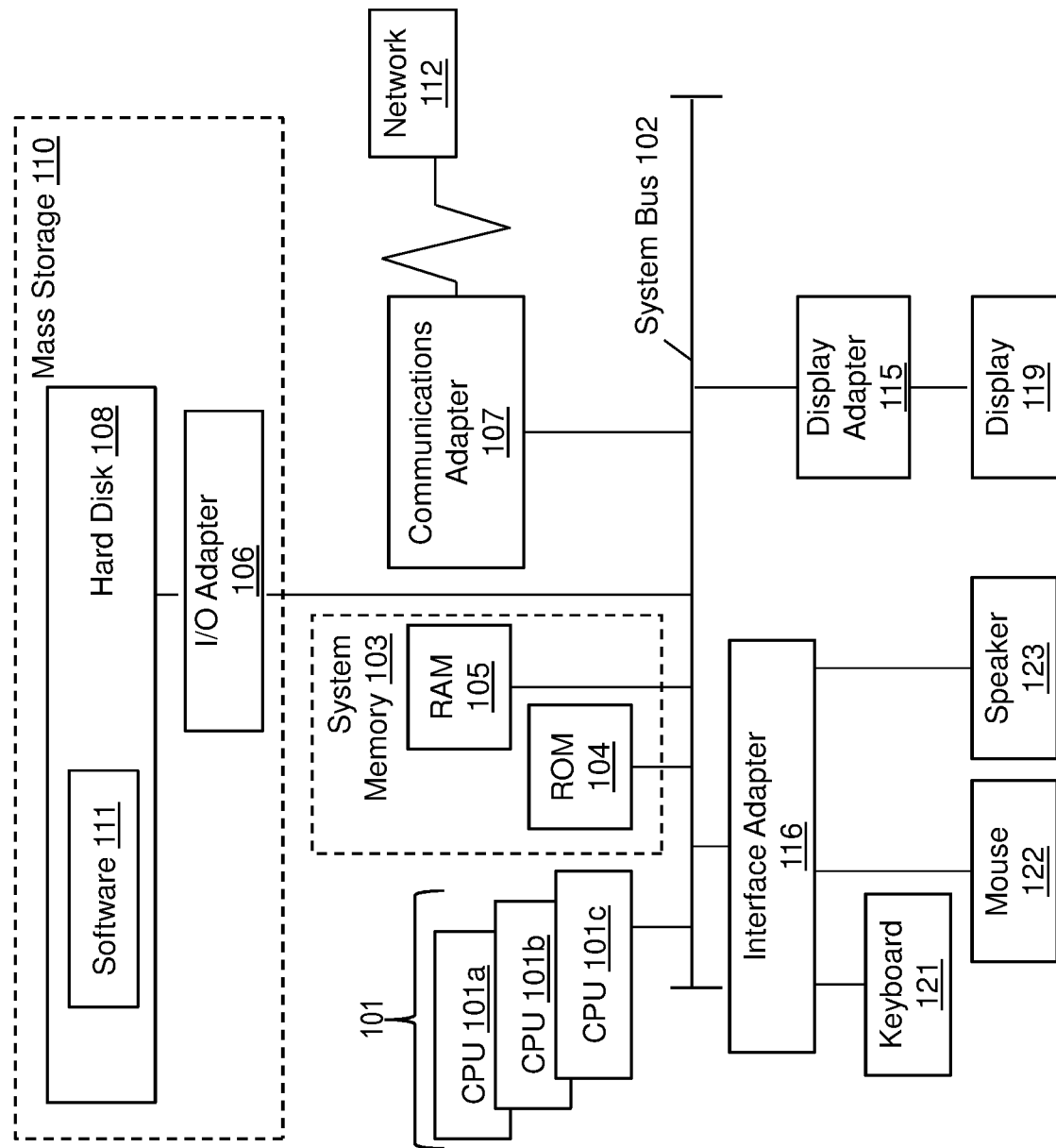
FIG. 1 depicts a block diagram of an example computer system for use in conjunction with one or more embodiments of the present invention.

Turning now to FIG. 1, a computer system 100 is generally shown in accordance with one or more embodiments of the invention. The computer system 100 can be an electronic, computer framework comprising and/or employing any number and combination of computing devices and networks utilizing various communication technologies, as described herein. The computer system 100 can be easily scalable, extensible, and modular, with the ability to change to different services or reconfigure some features independently of others. The computer system 100 may be, for example, a server, desktop computer, laptop computer, tablet computer, or smartphone. In some examples, computer system 100 may be a cloud computing node. Computer system 100 may be described in the general context of computer system executable instructions, such as program modules, being executed by a computer system. Generally, program modules may include routines, programs, objects, components, logic, data structures, and so on that perform particular tasks or implement particular abstract data types. Computer system 100 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, the computer system 100 has one or more central processing units (CPU(s)) 101a, 101b, 101c, etc., (collectively or generically referred to as processor(s) 101). The processors 101 can be a single-core processor, multi-core processor, computing cluster, or any number of other configurations. The processors 101, also referred to as processing circuits, are coupled via a system bus 102 to a system memory 103 and various other components. The system memory 103 can include a read only memory (ROM) 104 and a random access memory (RAM) 105. The ROM 104 is coupled to the system bus 102 and may include a basic input/output system (BIOS) or its successors like Unified Extensible Firmware Interface (UEFI), which controls certain basic functions of the computer system 100. The RAM is read-write memory coupled to the system bus 102 for use by the processors 101. The system memory 103 provides temporary memory space for operations of said instructions during operation. The system memory 103 can include random access memory (RAM), read only memory, flash memory, or any other suitable memory systems.

The computer system 100 comprises an input/output (I/O) adapter 106 and a communications adapter 107 coupled to the system bus 102. The I/O adapter 106 may be a small computer system interface (SCSI) adapter that communicates with a hard disk 108 and/or any other similar component. The I/O adapter 106 and the hard disk 108 are collectively referred to herein as a mass storage 110.

Software 111 for execution on the computer system 100 may be stored in the mass storage 110. The mass storage 110 is an example of a tangible storage medium readable by the processors 101, where the software 111 is stored as instructions for execution by the processors 101 to cause the computer system 100 to operate, such as is described herein below with respect to the various Figures. Examples of computer program product and the execution of such instruction is discussed herein in more detail. The communications adapter 107 interconnects the system bus 102 with a network 112, which may be an outside network, enabling the computer system 100 to communicate with other such systems. In one embodiment, a portion of the system memory 103 and the mass storage 110 collectively store an operating system, which may be any appropriate operating system to coordinate the functions of the various components shown in FIG. 1.

Additional input/output devices are shown as connected to the system bus 102 via a display adapter 115 and an interface adapter 116. In one embodiment, the adapters 106, 107, 115, and 116 may be connected to one or more I/O buses that are connected to the system bus 102 via an intermediate bus bridge (not shown). A display 119 (e.g., a screen or a display monitor) is connected to the system bus 102 by the display adapter 115, which may include a graphics controller to improve the performance of graphics intensive applications and a video controller. A keyboard 121, a mouse 122, a speaker 123, etc., can be interconnected to the system bus 102 via the interface adapter 116, which may include, for example, a Super I/O chip integrating multiple device adapters into a single integrated circuit. Suitable I/O buses for connecting peripheral devices such as hard disk controllers, network adapters, and graphics adapters typically include common protocols, such as the Peripheral Component Interconnect (PCI) and the Peripheral Component Interconnect Express (PCIe). Thus, as configured in FIG. 1, the computer system 100 includes processing capability in the form of the processors 101, and, storage capability including the system memory 103 and the mass storage 110, input means such as the keyboard 121 and the mouse 122, and output capability including the speaker 123 and the display 119.

In some embodiments, the communications adapter 107 can transmit data using any suitable interface or protocol, such as the internet small computer system interface, among others. The network 112 may be a cellular network, a radio network, a wide area network (WAN), a local area network (LAN), or the Internet, among others. An external computing device may connect to the computer system 100 through the network 112. In some examples, an external computing device may be an external webserver or a cloud computing node.

It is to be understood that the block diagram of FIG. 1 is not intended to indicate that the computer system 100 is to include all of the components shown in FIG. 1. Rather, the computer system 100 can include any appropriate fewer or additional components not illustrated in FIG. 1 (e.g., additional memory components, embedded controllers, modules, additional network interfaces, etc.). Further, the embodiments described herein with respect to computer system 100 may be implemented with any appropriate logic, wherein the logic, as referred to herein, can include any suitable hardware (e.g., a processor, an embedded controller, or an application specific integrated circuit, among others), software (e.g., an application, among others), firmware, or any suitable combination of hardware, software, and firmware, in various embodiments.

FIG. 2 depicts a block diagram of a system 200 for using patterned and correlated electrical activity and/or data of a user and other users to determine a medical event for the user in accordance with one or more embodiments of the present invention. FIG. 2 depicts one or more computers systems 202 coupled to numerous computer systems such as wearable devices 220 of a user and wearable devices 224 of other users co-located with the user of wearable devices 220. Co-located means that the other users wearing wearable device 224 are within and/or have been within a predefined distance of the user wearing wearable devices 220 while performing a synchronized activity. The predefined distance can be within about 5, 10, 20, 50, 100, 150, and/or 200 feet, or more. In one or more embodiments, a geofence can be utilized to implement the predefined distance such that the other users wearing wearable devices 224 and the user wearing wearable devices 220 are within the geofence. A geofence is a virtual perimeter for a real-world geographic area. The geofence could be a radius around a point location such as around the user wearing wearable devices 220 and/or a non-symmetrical shape. Further examples of co-location are discussed in FIG. 4.

Computer systems 202 can be representative of numerous computers in a datacenter and/or at the edge of a network 210. Elements of computer system 100 may be used in and/or integrated into computers system 202, wearable devices 220, and wearable devices 224 to function as discussed herein. In one or more embodiments, wearable devices 220 and wearable devices 224 can include communication software and hardware including receivers, transmitters, memory, software, etc., for communicating with computer system 202 via wireless and/or wired connections of network 210. In one or more embodiments, wearable devices 220 may be coupled to a mobile communication device 226 of the user and wearable devices 224 may be coupled to respective mobile communication devices 228 of the other users. Mobile communication device 226 and mobile communication devices 228 can be utilized to communicate with computer system 202 when wearable devices 220 and wearable devices 224 lack the communication capabilities. Examples of mobile communication device 226 and mobile communication devices 228 can include, but are not limited to, smartphones including cellular phones, tablets, laptops, home wireless/wired devices, computers, etc.

The types of wearable devices 220 and wearable devices 224, their placement on and/or to the body, and their capabilities including types and numbers of sensors are not meant to be limited. Examples of wearable devices 220 and wearable devices 224 may include but are not limited to fashion technology, smartwear, tech togs, skin electronics, smartwatches, spectacles, shoes, electronic textile-based cloths, etc. Wearable devices 220 and wearable devices 224 can be worn on and/or close to any part of the body including the extremities.

Figure 3B:
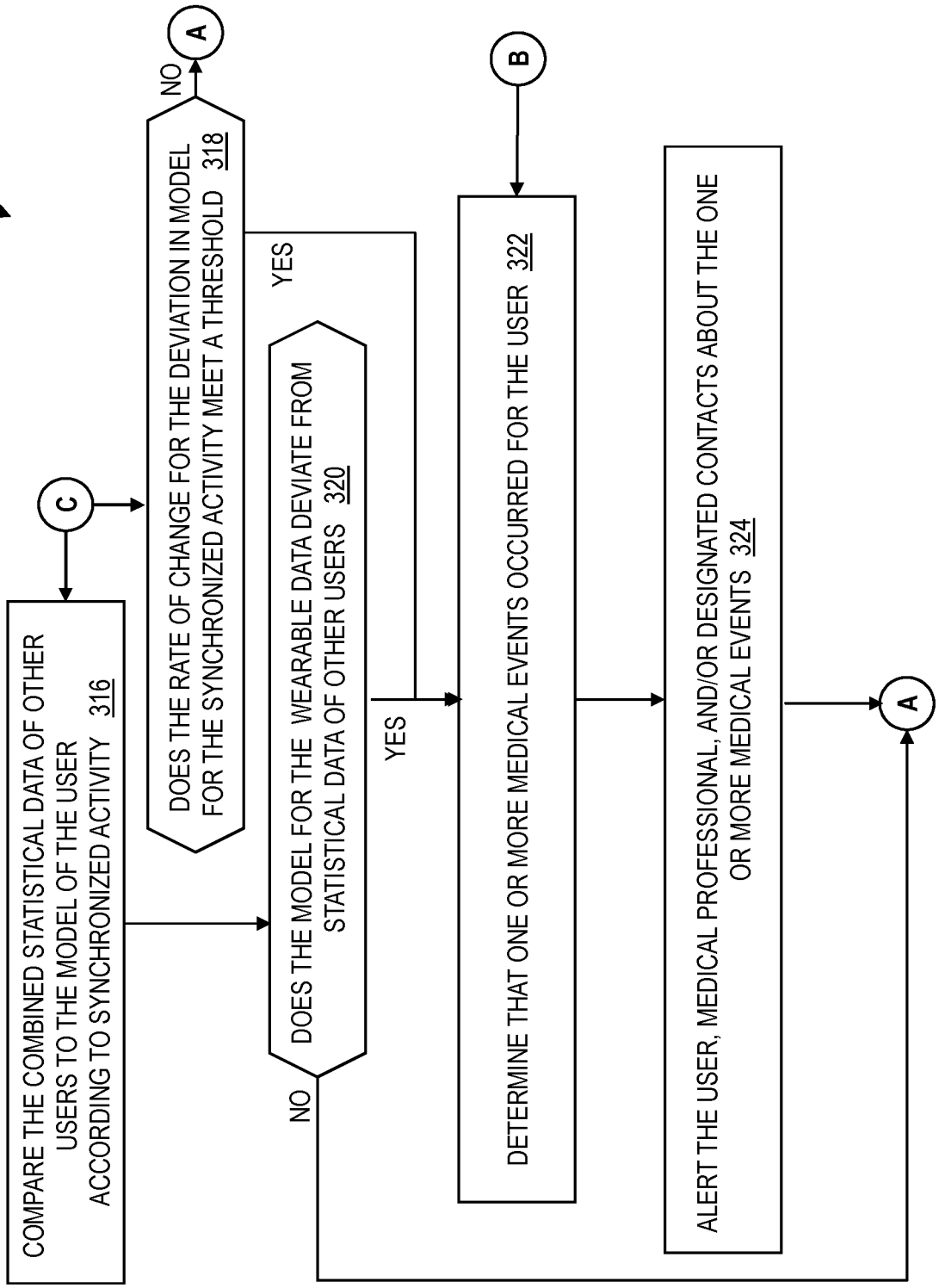

FIG. 3 illustrates a flowchart of a process 300 for using patterned and correlated electrical activity or data of a user being evaluated and other users to determine a medical event for the user in accordance with one or more embodiments of the present invention. Process 300 in FIGS. 3A and 3B will be described with reference to FIG. 2. At block 302, software applications 204 on computer system 202 are configured to request and/or receive wearable device data of one or more wearable devices 220 worn and/or utilized by a user and wearable device data of wearable devices 224 for other users co-located with the user. The wearable device data of wearable device 220 and wearable devices 224 may be stored in database 230 in memory 206. Database 230 may contain hundreds, thousands, and/or millions of pieces of data, also referred to as "big data". In accordance with one or more embodiments, the enormous size of database 230 requires management, processing, searching, etc., by a machine (such as computer system 202), for example, using computer-executable instructions and could not be practically managed, stored, analyzed, and/or processed as discussed herein within the human mind.

Wearable devices 220 and wearable devices 224 may communicate directly with computer system 202 and/or communicate with their respective mobile communication device 226 and mobile communication devices 228, which then transit the corresponding wearable device data to computer system 202. Wearable devices 220, wearable devices 224, mobile communication device 226, and mobile communication devices 228 can interface directly with software application 204 of computer system 202 and/or use a client application 222 to interface with software application 204. Although included, client application 222 is not shown in mobile communication device 226 and mobile communication devices 228 for the sake of conciseness. Software application 204 may be implemented as software 111 executed on one or more processors 101, as discussed in FIG. 1. Similarly, client application 222 may be implemented using software 111 configured to execute on one or more processors 101. Client application 222 may include cookies, plug-ins, etc. In one or more embodiments, client application 222 may further serve as a piece of computer software that places wearable device data in a structure useable by software applications 204 of computer system 202. In one or more embodiments, software applications 204 are configured to format the wearable device data into a suitable structure.

At block 304, software applications 204 on computer system 202 are configured to classify the collected wearable device data of wearable devices 220 of the user and also classify the collected wearable data of wearable devices 224 of the other users. The collected wearable device data of wearable devices 224 and wearable devices 220 are classified into one or more synchronized activities. Additionally, wearable device data on wearable devices 224 of other users is checked by software applications 204 to confirm if it is the same type of wearable device data measured and collected from wearable device 220 of the user. If not, such wearable device data of the other users is discarded. This ensures that wearable devices of the same type and same portion of the body will be compared such as, for example, software applications 204 will compare wearable device data of a wristwatch with another wristwatch, wearable device data of a shoe with wearable device data of another shoe, and so forth.

The wearable device data from wearable devices 224 of other users is crowdsourced data and is obtained by computer system 202 because wearable devices 224 are co-located with wearable device 220 as discussed herein. The other users are co-located with the user because of a social interaction area which could be an unplanned social interaction and/or a planned social interaction area. As a geofence, the predefined distance or proximity between the user of wearable devices 220 and the other users of wearable devices 224 can be increased to encompass more wearable devices 224 and/or decreased to encompass fewer wearable devices 224. In addition to selecting wearable devices in a geofence/predetermined area, co-located wearable devices from multiple users may be collaborating with each other and sharing data with each other for comparison, and software applications 205 may select/include wearable devices based on the wearable devices collaborating with one another, in one or more embodiments.

FIG. 4 depicts a block diagram of a social interaction area 400 according to one or more embodiments of the invention. The social interaction area 400 includes one or more wearable devices 220 of the user being evaluated along wearable devices 224 of various other users where one or more synchronized social activities occur. A synchronized activity in an activity that can be performed in unison or nearly in unison, an activity that is uniform, and/or an activity that has a uniform exchange even though not performed in unison (e.g., speaking in a conversation). Examples of synchronized social activities can include but are not limited to people engaging in social interactions while watching sports in a stadium such as chanting the same chant, singing the same song, clapping to a rhythm, performing a gesture (e.g., a wave, arm motion, standing and sitting) in a uniform and/or staggered fashion, etc. Further, examples of synchronized social activities can include people jogging in generally the same direction, walking in generally the same, singing the same song in a choir, etc. During classification, software applications 204 are configured to increase and/or decrease the size of a predetermined area and/or geofence of other users to be utilized for comparison with the user. Although software applications 204 can receive wearable device data from all of the wearable devices 224 of other users as well as wearable device 220 of the user depicted in FIG. 4, software applications 204 are configured to increase or decrease the area/geofence of wearable devices 224 to any of the example areas/geofences which are illustrated as areas/geofences 402A, 402B, 402C in FIG. 4, such that more or fewer wearable devices 224 are to be utilized in the comparison. As such, some wearable device data of wearable devices 224 can be eliminated from further processing according to the size of the areas/geofences. Areas/geofences 402A, 402B, 402C can generally be referred to as area/geofence 402. Software applications 204 are configured to obtain general location information regarding wearable device 220 of the user, and with this location information, software applications 204 can determine the type of social interaction area 400 which helps to determine the type of social activity. For example, the user can be located in a sports stadium according to location information (e.g., according to GPS on a phone, local WiFi hotspots, etc.), and software applications 204 may select a rectangular area/geofence 402C which represents the side of the home team where synchronized activities would occur. Wearable devices 224 in the selected area/geofence 402 are used for classification. As more explanation of block 304, FIG. 5 depicts a process 500 of further details for classifying the wearable device data of the user and other users according to one or more embodiments of the invention. Software applications 204 may include, integrate, and/or employ one or more classification engines 232 to help classify the wearable device data. At block 502, software applications 204 are configured to categorize wearable device data of the user according to the type of wearable devices 220 being utilized by the user. The user may be wearing one or more types of wearable devices 220. For example, a person can have multiple IoT sensors or wearable devices including smartwatch, spectacles, shoes, electronic textile-based clothing, etc. Along with determining the type of wearable device, software applications 204 determine capabilities of each wearable devices in preparation for comparison with other users and elimination of wearable device data of a different type from the user. Similarly, at block 504, software applications 204 are configured to categorize wearable device data of the other users according to the type of wearable devices 224 being utilized by other users. Additionally, software applications 204 are configured to purge wearable device data of other users which do not match the types of wearable devices 220 being utilized by the user. In order for the same type of wearable device data of wearable devices 224 to be compared with wearable device data of wearable device 220 for the same synchronized activity at the same social interaction.

At block 506 in FIG. 5, software applications 204 are configured to check the wearable device data of the user and other users for a unique usage pattern because the unique usage pattern is indicative of a synchronized activity. The usage pattern defines user movement and/or physical user action (such as speaking) over time. Any wearable device data of other users having no unique usage pattern indicative of a synchronized activity is discarded at block 508. In preparation for classification, the collected wearable device data of other users and the user can be placed in a structured format by software applications 204, if not initially received in a structured format. FIG. 6 depicts an example of wearable device data in a structured format 600 according to one or more embodiments of the invention. Although software applications 204 can anonymize wearable device data of other users as depicted in structured format 600, it should be appreciated that wearable device data for the user being evaluated is not anonymized. Each wearable device 220 and wearable device 224 collects data over time, based on the type of sensor(s), i.e., the type of wearable device. For example, user movement and/or physical user action are tracked over time which can correspond to an output over time, and this output is utilized to determine the usage pattern. Examples of the output measured over time can include electrical/energy output, position/positional output, acceleration output, acoustical output, etc., measured and collected by wearable devices, and this output may be in conjunction with various biometrics when available. FIG. 6 illustrates time and measured output in the second row of the structed format 600. For explanation purposes, the measured output has a time such as "t0" and measured value such as "X" units, where the units can be meters, feet, inches, etc., when measuring position or movement. It should be appreciated that any suitable units are utilized according to the capability of the sensor and what is being measured. When checking for unique usage patterns in the wearable device data associated with a synchronized activity and parsing through the output of the wearable device data to determine how the output changes over time, software applications 204 are configured to detect any repeating patterns and determine how the patterns correlate among users. For example, software applications 204 may detect "J" amount of movement for "K" number of microseconds. When a unique usage pattern is found, at block 510, software applications 204 are configured to classify the usage pattern of the wearable device data of the user and other users according to one or more synchronized activities. In one or more embodiments, software applications 204 may access mapping 240 to may the usage pattern for a given part of the body to a specific synchronized activity. In some cases, the user may be wearing more than one wearable device 220 and/or the wearable device 220 can has more than one sensor, such that more than one synchronized activity can be tracked. Accordingly, software applications 204 are configured to process the wearable device data for each of the wearable devices 220 and/or sensors of wearable device 220, to determine more than one synchronized activity (e.g., both clapping and standing/rocking, chanting with arm movements, etc.). Although not explicitly shown in FIG. 5, one or more blocks in process 500 of FIG. 5 can be simultaneously and/or nearly simultaneously processed with one or more blocks in FIGS. 3A and 3B for multiple types of wearable device data.

The features of classification engines 232 as well as diagnosis classifier 238 described herein can be implemented on computer system 202 shown in FIG. 2 or can be implemented on a neural network (not shown) that can be coupled to computer system 202. In one or more embodiments of the invention, the features of classification engines 232 (and diagnosis classifier 238) can be implemented by configuring and arranging computer system 202 to execute machine learning (ML) algorithms. In general, ML algorithms, in effect, extract features from received data (e.g., inputs to classification engines 232 and/or diagnosis classifier 238) in order to "classify" the received data. Examples of suitable classifiers include but are not limited to neural networks (described in greater detail below), support vector machines (SVMs), logistic regression, decision trees, hidden Markov Models (HMMs), etc. The end result of the classifier's operations, i.e., the "classification," is to predict a class for the data. The ML algorithms apply machine learning techniques to the received data in order to, over time, create/train/update a unique "model." The learning or training performed by the classification engines 232 (and diagnosis classifier 238) can be supervised, unsupervised, or a hybrid that includes aspects of supervised and unsupervised learning. Supervised learning is when training data is already available and classified/labeled. Unsupervised learning is when training data is not classified/labeled so must be developed through iterations of the classifier. Unsupervised learning can utilize additional learning/training methods including, for example, clustering, anomaly detection, neural networks, deep learning, and the like. In embodiments of the invention where classification engines 232 (and/or diagnosis classifier 238) are implemented as neural networks, a resistive switching device (RSD) can be used as a connection (synapse) between a pre-neuron and a post-neuron, thus representing the connection weight in the form of device resistance. Neuromorphic systems are interconnected processor elements that act as simulated "neurons" and exchange "messages" between each other in the form of electronic signals. Similar to the so-called "plasticity" of synaptic neurotransmitter connections that carry messages between biological neurons, the connections in neuromorphic systems such as neural networks carry electronic messages between simulated neurons, which are provided with numeric weights that correspond to the strength or weakness of a given connection. The weights can be adjusted and tuned based on experience, making neuromorphic systems adaptive to inputs and capable of learning. For example, a neuromorphic/neural network for handwriting recognition is defined by a set of input neurons, which can be activated by the pixels of an input image. After being weighted and transformed by a function determined by the network's designer, the activations of these input neurons are then passed to other downstream neurons, which are often referred to as "hidden" neurons. This process is repeated until an output neuron is activated. Thus, the activated output neuron determines (or "learns") which character was read. Multiple pre-neurons and post-neurons can be connected through an array of RSD, which naturally expresses a fully-connected neural network.

Figure 7:
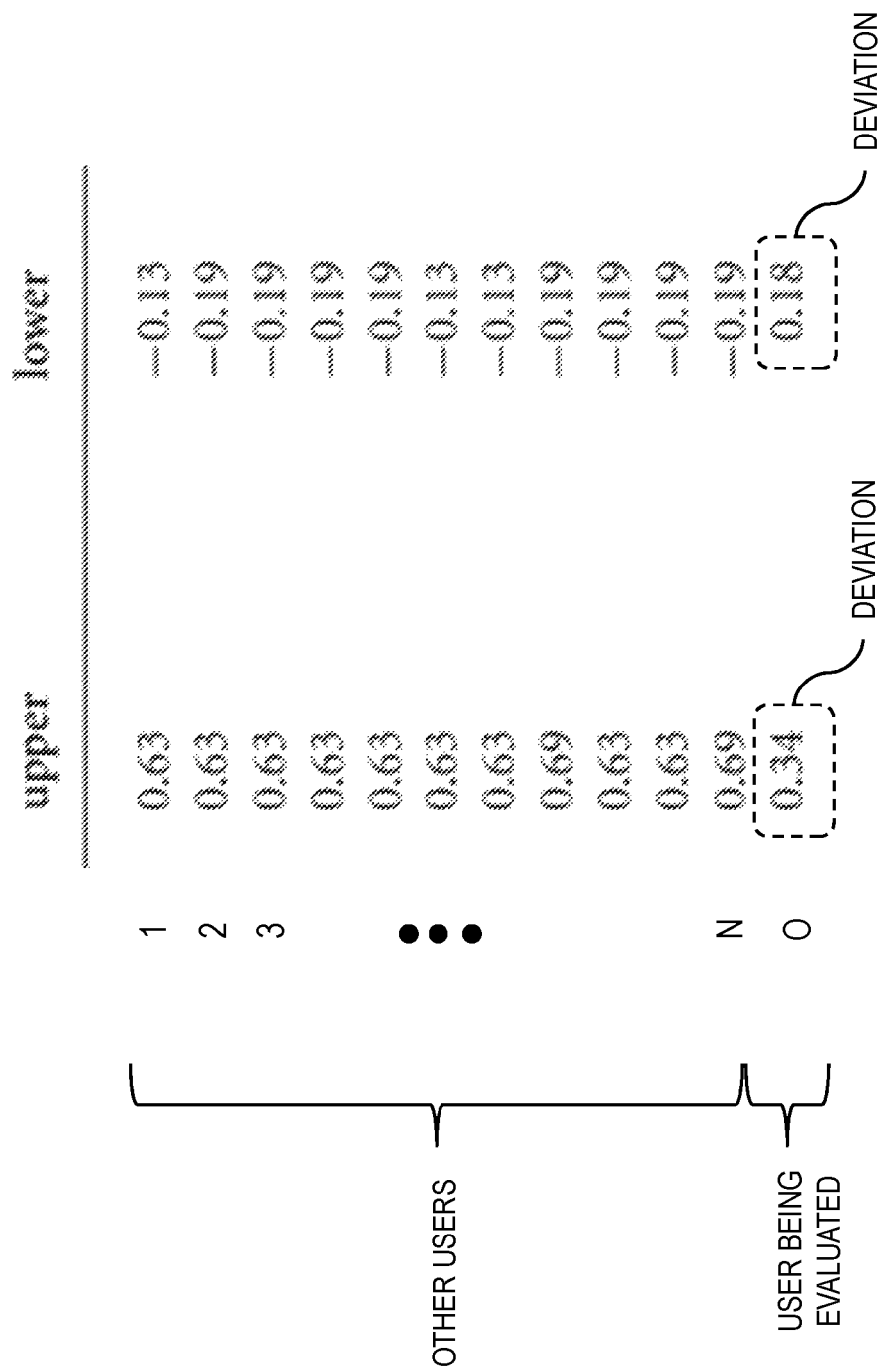
FIG. 7 depicts output from wearable device data representing usage patterns with upper and lower limits for a synchronized activity in accordance with one or more embodiments of the present invention.

Referring back to FIG. 3, at block 306, software applications 204 are configured to correlate the wearable device data of the user and the other users for a given start time related to the synchronized activity and compare the correlated wearable device data of the other users to the user at block 308. The user and other users are not required to all have the same start time in their respective wearable device data; instead software applications 204 determines the appropriate start time for each such that the synchronized activity aligns. For example, software applications 204 are configured to align the usage pattern in the wearable device data of the user and the other users at a given start time. For explanation purposes, the synchronized activity is determined to be clapping hands in a synchronized manner, and the synchronized activity has a unique usage pattern captured by wearable devices 224 and wearable device 220. The usage pattern may represent repeated movements/motions of moving hands to open and close the distance between hands, thus signifying repeated hand clapping. Software applications 204 correlate the usage pattern for the wearable device data by defining a start time and aligning all wearable device data to start when, for example, the hands move away from each other (which may be a valley in a waveform of the signal) or when the hands close to clap (which may be a peak in the waveform of the signal) (or vice versa). Either way, if at the instant some users are closing their hands together to the minimal distance of separation for the clap while other users are opening their hands to the maximum distance of separation for the clap, this difference does not affect the comparison, because the syncopation or spacing of time between claps should be about the same from the minimal distance back to the maximum distance and vice versa; therefore, aligning the start time for the usage pattern in the wearable device data of the user and other users eliminates any errors (e.g., regarding a difference in clapping on the downbeat versus the upbeat as long as the user is in rhythm), thereby allowing software applications 204 to compare the usage pattern of the user and other users participating in the synchronized activity of clapping on rhythm (i.e., in time) for the song, cheer, chant, and/or fanfare being played during the social interaction (e.g., a sporting event). Accordingly, software applications 204 compare the usage pattern of the user for the synchronized activity to the usage pattern for the other users to determine deviations at block 310. When the usage pattern of the user deviates from the usage pattern of the other users for the synchronized activity greater than a predefined short-term threshold, flow proceeds to block 322; otherwise, flow proceeds to block 312 discussed further below. Optionally, flow may continue to block 312 even when the determinization is "Yes" at block 310. The short-term threshold may be set to identify immediate changes to the user as compared to the other users for an individual social interaction (e.g., a single data set). The short-term thresholds for a given synchronized activity is set to values that may be different from long-terms thresholds for the same synchronized activity over many different social interactions (i.e., numerous data sets), in order to detect sudden changes in the user's ability to synchronize with behavior of other users during a synchronized social interaction, indicative of an immediate onset of a health issue and/or a sudden degradation in health. Example measured output of wearable device data which has been aligned in time is depicted for wearable devices 224 of other users and wearable device 220 of the user being evaluated in FIG. 7. In the example depicted in FIG. 7, the output from wearable device data representing the usage pattern has upper and lower limits which could be for any type of synchronized activity such as, for example, head movement, hand clapping, arm movement, leg movement, etc., and this example is for a particular data set. For example, FIG. 7 may be for a data set of wearable device data collected at a single social interaction. In one or more embodiments, the upper limit and lower limit can be averages of upper limits and lower limits for each respect other user and the user. By comparing the upper and lower limits of wearable device data for the other users to the upper and lower limits of wearable device data for the user being evaluated, software application 204 determine that there are deviations or differences in the upper limit and lower limit for the synchronized activity. When the deviation of the upper limit, lower limit, and/or both are greater than their respective predefined short-term thresholds, software applications 204 are configured to proceed to block 322 as discussed herein.

Referring back to FIG. 3, when the usage pattern of the user deviates from the usage pattern of the other users for the synchronized activity less than a predefined short-term threshold, software applications 204 on computer system 202 are configured to generate a new user model 234 for the synchronized activity (e.g., this is the first time the synchronized activity has been detected for the user) and/or update an existing user model 234 for the synchronized activity with the deviation (e.g., synchronized activity has previously been detected for the user) at block 312. User model 234 is generated for each type of synchronized activity such that the user's behavior can be tracked over time to determine if the user is developing and/or has developed a problem. Also, at block 314, software applications 204 on computer system 202 are configured to combine statistical data for wearable devices 224 of the other users over time for each synchronized activity and compare to the combined statistical data to user model 234 for the synchronized activity at block 316. For each synchronized activity, the statistical data of wearable devices 224 for other users can include the mean, probability distribution, standard deviation, etc. At block 320, software applications 204 on computer system 202 are configured to determine whether user model 234 of deviations for the synchronized activity deviates from the combined statistical data of other users for the same synchronized activity. When differences between the user model 234 of deviations of the wearable device data for the synchronized activity and combined statistical data of deviations for other users is greater than a long-term threshold, software applications 204 on computer system 202 are configured to determine that one or more medical events occurred for the user at block 322. At block 324, software applications 204 on computer system 202 are configured to alert the user of the medical event on mobile communication device 226, alert a medical professional on a system or communication device, and/or alert designated contact on communication devices. The alert can be an automated phone call describing the possible medical event, a text message, an entry in a database that further alerts medical personnel, a sound on a mobile communication device, etc. Additionally, at block 318, software applications 204 on computer system 202 are configured to check whether the rate of change for the deviation in the user model 234 for the synchronized activity exceeds a rate of change threshold. If yes, flow proceeds to block 322 where processing occurs as discussed herein. If no, flow proceeds block 302.

In addition to determining that one or more medical events occurred and alerting the user, medical professional, and designated contacts as discussed herein, software diagnosis classifier 238 is configured to diagnose the one or more medical events by providing and transmitting a suggestion and/or possible diagnosis of the medical event to the user, medical professional, and/or designated contacts along with the alert of the medical event. Software applications 204 may include, integrate, and/or employ diagnosis classifier 238. Diagnosis classifier 238 can use predictive modeling to suggest/provide the possible diagnosis of the medical event. After wearable device data (or logs) from wearable devices 224 and wearable device 220 are correlated and used to identify a deviation in wearable device data of the user being evaluated (whether a sudden change and/or over a period of a time), software applications 204 predict whether the user is having a synchronization problem with other users. After the comparative analysis of wearable device data identifies delays in responding and/or the amount of deviation in the social synchronization, software applications 204 predict the rate of change in the synchronization problem of the user, and additionally, software applications 204 determine a seriousness factor. Based on the position of the body and type of signals (wearable device data) from different portions of the body, software applications 204 identify what type of synchronization problem the user is experiencing. For instance, when the user is not able to synchronize clapping and/or walking, software applications 204 may determine that the synchronization problem is related to hearing or visual cognition of the user.

Figure 8:
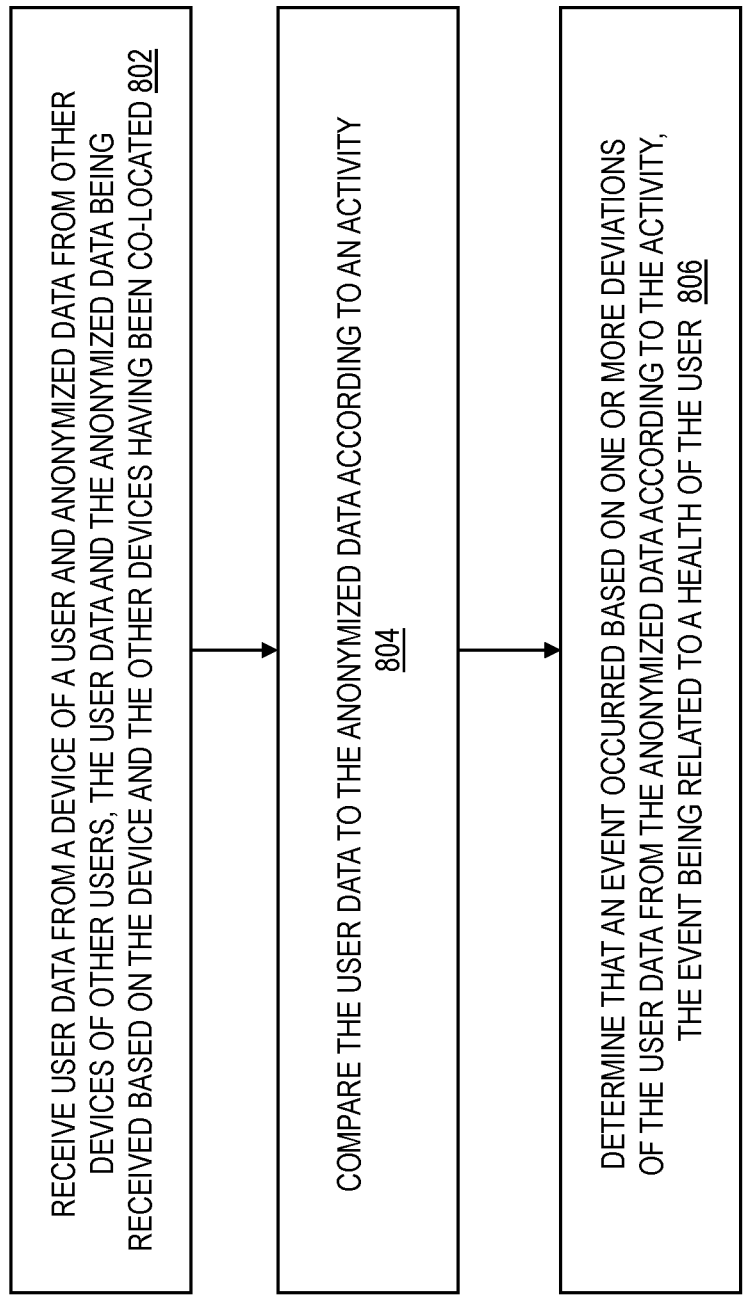
FIG. 8 is a flowchart of a computer-implemented method using patterned and correlated electrical activity and/or wearable device data of a user and other users to determine a medical event for the user being evaluated in accordance with one or more embodiments of the present invention.

FIG. 8 is a flowchart of a computer-implemented method 800 for using patterned and correlated electrical activity and/or wearable device data of a user and other users to determine a medical event for the user being evaluated in accordance with one or more embodiments of the present invention. At block 802, software applications 204 are configured to receive user data (e.g., wearable device data from wearable device 220) from a device of a user and anonymized data (e.g., wearable device data from wearable devices 224) from other devices of other users, the user data and the anonymized data being received based on the device and the other devices having been co-located. For example, being co-located can include example areas/geofences 402A, 402B, 402C representing geographical locations encompassing and/or approximately encompassing wearable device 224 with wearable device 220. At block 804, software applications 204 are configured to compare the user data to the anonymized data according to an activity. The activity is a synchronized activity intended to be performed in unison and/or nearly in unison by the user and other co-located users, each of which is wearing a wearable device capable of sensing and capturing wearable device data indicative of the activity. At block 806, software applications 204 are configured to determine that an event occurred based on one or more deviations of the user data from the anonymized data according to the activity, the event being related to a health of the user.

The device (e.g., wearable device 220) of the user and the other devices (e.g., wearable devices 224) comprise wearable devices. The wearable devices can be on any portion of the body including extremities. The user data and the anonymized data are related to the activity, the user data being intended to have a synchronization with the anonymized data for the activity. For example, the user data and anonymized data are both related to a synchronized activity such as, for example, clapping. The user data and the anonymized data are related to one or more audible activities (e.g., speaking, singing, chanting, etc.), one or more movement activities (e.g., moving any part of the body including extremities), or a combination of the one or more audible activities and the one or more movement activities. The one or more deviations of the user data from the anonymized data is representative of a problem in a synchronization of the activity between the user and the other users. The one or more deviations of the user data from the anonymized data is diagnosed as a medical event.

Determining that the event occurred based on the one or more deviations of the user data from the anonymized data according to the activity comprises meeting one or more short-term thresholds (e.g., block 310), meeting one or more long-term thresholds (e.g., block 316 and/or block 318), or a combination of both meeting the one or more short-term thresholds and meeting the one or more long-term thresholds (e.g., any combination of block 310 with block 316 and/or 318). The one or more long-term thresholds are associated with an aggregation of the one or more deviations with previous deviations (e.g., in a user model 234) for the user related to the activity.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 9:
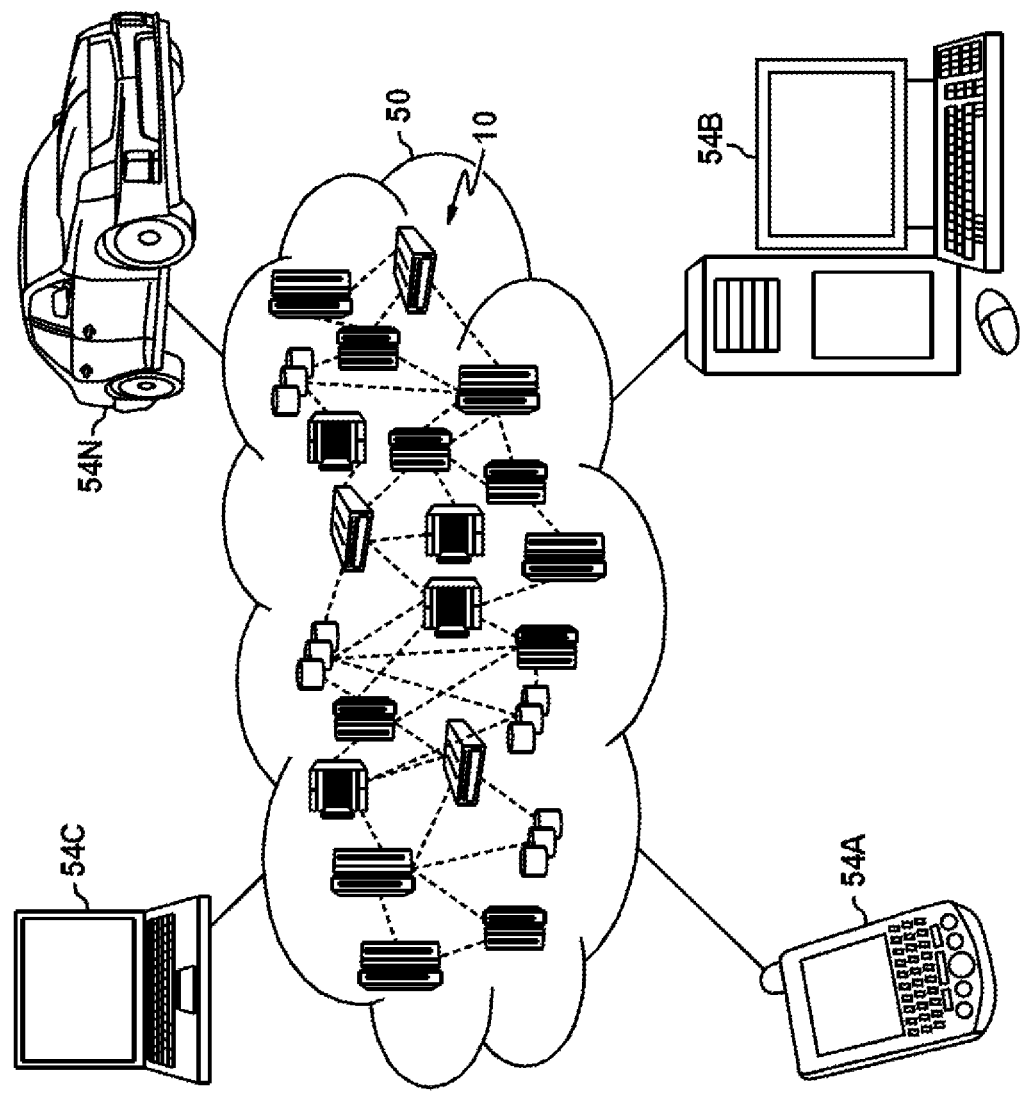
FIG. 9 depicts a cloud computing environment according to one or more embodiments of the present invention.

Referring now to FIG. 9, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described herein above, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 9 are intended to be illustrative only and that computing nodes 10 and cloud computing environment 50 can communicate with any type of computerized device over any type of network and/or network addressable connection (e.g., using a web browser).

Figure 10:
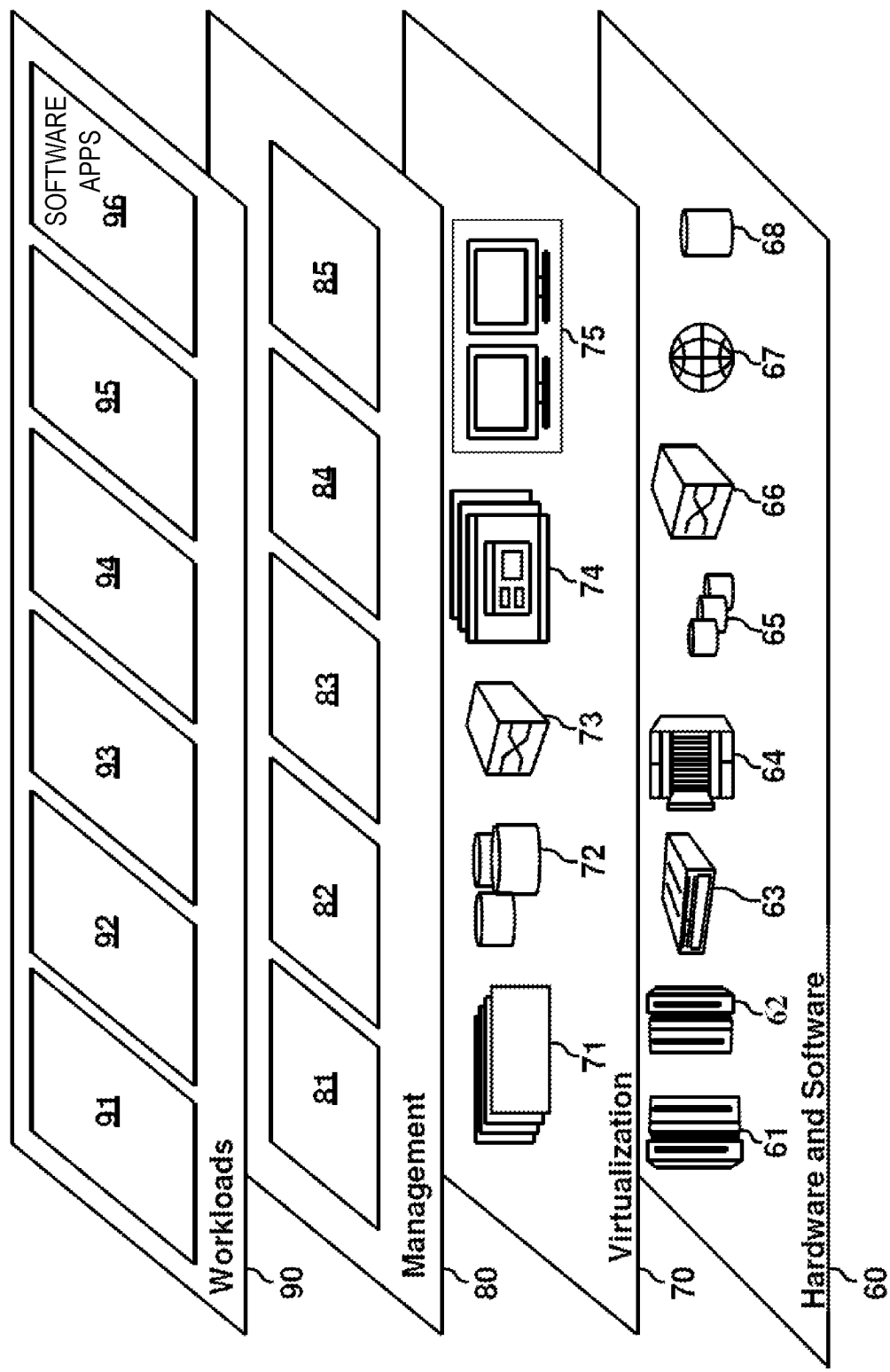
FIG. 10 depicts abstraction model layers according to one or more embodiments of the present invention.

Referring now to FIG. 10, a set of functional abstraction layers provided by cloud computing environment 50 (FIG. 9) is shown. It should be understood in advance that the components, layers, and functions shown in FIG. 10 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and software applications (e.g., software applications 204, classification engines 232, and diagnosis classifier 238) implemented in workloads and functions 96.

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

One or more of the methods described herein can be implemented with any or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

In some embodiments, various functions or acts can take place at a given location and/or in connection with the operation of one or more apparatuses or systems. In some embodiments, a portion of a given function or act can be performed at a first device or location, and the remainder of the function or act can be performed at one or more additional devices or locations.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The present disclosure has been presented for purposes of illustration and description, but is not intended to be exhaustive or limited to the form disclosed. Many modifications and variations will be apparent to those of ordinary skill in the art without departing from the scope and spirit of the disclosure. The embodiments were chosen and described in order to best explain the principles of the disclosure and the practical application, and to enable others of ordinary skill in the art to understand the disclosure for various embodiments with various modifications as are suited to the particular use contemplated.

The diagrams depicted herein are illustrative. There can be many variations to the diagram or the steps (or operations) described therein without departing from the spirit of the disclosure. For instance, the actions can be performed in a differing order or actions can be added, deleted or modified. Also, the term "coupled" describes having a signal path between two elements and does not imply a direct connection between the elements with no intervening elements/ connections therebetween. All of these variations are considered a part of the present disclosure.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are understood to include any integer number greater than or equal to one, i.e. one, two, three, four, etc. The terms "a plurality" are understood to include any integer number greater than or equal to two, i.e. two, three, four, five, etc. The term "connection" can include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A computer-implemented method comprising:
   receiving user data from a wearable device of a user and anonymized data from other wearable devices of other users, the user data and the anonymized data being received based on the wearable device and the other wearable devices having been at a same location performing a synchronized activity, the synchronized activity comprising a gesture intended to be performed in unison by the user and the other users; the synchronized activity further comprising moving in a uniform or staggered motion by the user and the other users;
   comparing the user data to the anonymized data according to the synchronized activity of the gesture intended to be performed in unison with the user and the other users; and
   determining that an event occurred based on one or more deviations of the user data from the anonymized data according to the synchronized activity, the event being related to a health of the user.

2. The computer-implemented method of claim 1, wherein the user data and the anonymized data are further related to one or more audible activities, one or more movement activities, or a combination of the one or more audible activities and the one or more movement activities.

3. The computer-implemented method of claim 1, wherein the one or more deviations of the user data from the anonymized data is representative of a problem in a synchronization of the synchronized activity between the user and the other users.

4. The computer-implemented method of claim 1, wherein the one or more deviations of the user data from the anonymized data is diagnosed as a medical event.

5. The computer-implemented method of claim 1, wherein determining that the event occurred based on the one or more deviations of the user data from the anonymized data according to the synchronized activity comprises meeting one or more short-term thresholds, meeting one or more long-term thresholds, or a combination of both meeting the one or more short-term thresholds and meeting the one or more long-term thresholds; and wherein the one or more long-term thresholds are associated with an aggregation of the one or more deviations with previous deviations for the user related to the synchronized activity.

6. A system comprising:
   a memory having computer readable instructions; and
   one or more processors for executing the computer readable instructions, the computer readable instructions controlling the one or more processors to perform operations comprising:
   receiving user data from a wearable device of a user and anonymized data from other wearable devices of other users, the user data and the anonymized data being received based on the wearable device and the other wearable devices having been at a same location performing a synchronized activity, the synchronized activity comprising a gesture intended to be performed in unison by the user and the other users; the synchronized activity further comprising moving in a uniform or staggered motion by the user and the other users;
   comparing the user data to the anonymized data according to the synchronized activity of the gesture intended to be performed in unison with the user and the other users; and
   determining that an event occurred based on one or more deviations of the user data from the anonymized data according to the synchronized activity, the event being related to a health of the user.

7. The system of claim 6, wherein the user data and the anonymized data are further related to one or more audible activities, one or more movement activities, or a combination of the one or more audible activities and the one or more movement activities.

8. The system of claim 6, wherein the one or more deviations of the user data from the anonymized data is representative of a problem in a synchronization of the synchronized activity between the user and the other users.

9. The system of claim 6, wherein the one or more deviations of the user data from the anonymized data is diagnosed as a medical event.

10. The system of claim 6, wherein determining that the event occurred based on the one or more deviations of the user data from the anonymized data according to the synchronized activity comprises meeting one or more short-term thresholds, meeting one or more long-term thresholds, or a combination of both meeting the one or more short-term thresholds and meeting the one or more long-term thresholds; and
    wherein the one or more long-term thresholds are associated with an aggregation of the one or more deviations with previous deviations for the user related to the synchronized activity.

11. A computer program product comprising a non-transitory computer readable storage medium having program instructions embodied therewith, the program instructions executable by a processor to cause the processor to perform operations comprising:

receiving user data from a wearable device of a user and anonymized data from other wearable devices of other users, the user data and the anonymized data being received based on the wearable device and the other wearable devices having been at a same location performing a synchronized activity, the synchronized activity comprising a gesture intended to be performed in unison by the user and the other users; the synchronized activity further comprising moving in a uniform or staggered motion by the user and the other users;

comparing the user data to the anonymized data according to the synchronized activity of the gesture intended to be performed in unison with the user and the other users; and determining that an event occurred based on one or more deviations of the user data from the anonymized data according to the synchronized activity, the event being related to a health of the user.

12. The computer program product of claim 11, wherein the user data and the anonymized data are further related to one or more audible activities, one or more movement activities, or a combination of the one or more audible activities and the one or more movement activities.

13. The computer program product of claim 11, wherein the one or more deviations of the user data from the anonymized data is representative of a problem in a synchronization of the synchronized activity between the user and the other users.

14. The computer program product of claim 11, wherein the one or more deviations of the user data from the anonymized data is diagnosed as a medical event.

\* \* \* \* \*